(12) United States Patent
Khavinson et al.

(10) Patent No.: US 7,189,701 B1
(45) Date of Patent: Mar. 13, 2007

(54) TETRAPEPTIDE STIMULATING FUNCTIONAL ACTIVITY OF NEURONS PHARMACOLOGICAL AGENT BASED THEREON AND METHOD OF USE THEREOF

(75) Inventors: Vladimir K. Khavinson, St. Petersburg (RU); Vyacheslav G. Morozov, Leningradskaya obl. (RU); Vladimir V. Malinin, St. Petersburg (RU); Evgeny I. Grigoriev, St. Petersburg (RU)

(73) Assignee: Sankt-Petersburgskaya Obschestvennaya Organizatsiya "Institut Bioregulyatsii I Gerontologii Szo Ramn", St. Petersburg (RU)

( * ) Notice: Subject to any disclaimer, the term of this patent is extended or adjusted under 35 U.S.C. 154(b) by 0 days.

(21) Appl. No.: 10/110,981

(22) PCT Filed: May 25, 2000

(86) PCT No.: PCT/RU00/00218

§ 371 (c)(1),
(2), (4) Date: Sep. 20, 2002

(87) PCT Pub. No.: WO01/29067

PCT Pub. Date: Apr. 26, 2001

(30) Foreign Application Priority Data

Oct. 20, 1999 (RU) .................................. 99121778

(51) Int. Cl.
*A61K 38/00* (2006.01)
(52) U.S. Cl. ............................ 514/18; 514/2; 530/330; 546/200
(58) Field of Classification Search ................... 514/2, 514/18; 530/330; 546/200
See application file for complete search history.

*Primary Examiner*—B. Dell Chism
(74) *Attorney, Agent, or Firm*—Whitham, Curtis, Christofferson & Cook, PC

(57) ABSTRACT

Tetrapeptide L-alanyl-L-glutamyl-L-asparagyl-L-proline of the general formula L-Ala-L-Glu-Asp-L-Pro is proposed as a biologically active compound stimulating the functional activity of neurones. The application of L-Ala-L-Glu-L-Asp-L-Pro tetrapeptide in medicine is proposed for the preparation of a drug stimulating the functional activity of neurones. There is proposed a pharmacological agent, which contains as its active base an effective amount of L-Ala-L-Glu-L-Asp-L-Pro tetrapeptide for its salts of the amino acid group (acetate, hydrochloride, oxalate) or its salts of carboxyl groups (the salts of sodium, potassium, calcium, lithium, zinc, magnesium, and also the salts of organic and inorganic cations-ammonium, triethylammonium). The agent is proposed for parenteral, intranasal and oral administration. In accordance with the invention, the method of stimulating the functional activity of neurones consists in preventive and/or therapeutic administration to the patient of the pharmacological agent in doses 0.01 to 100 μg/kg of the body weight at least one a day for a period necessary for attaining a therapeutic effect.

11 Claims, 3 Drawing Sheets

TETRAPEPTIDE STIMULATING FUNCTIONAL ACTIVITY OF NEURONS PHARMACOLOGICAL AGENT BASED THEREON AND METHOD OF USE THEREOF

FIELD OF THE INVENTION

The present invention relates to medicine and is intended to be used as an agent stimulating functional activity of neurones in central nervous system diseases and traumas.

BACKGROUND OF THE INVENTION

There are known several medicinal agents like Pyracetam, Aminalon, Pyriditol, Pantogam, Sodium Oxybutyrate, etc. (1) stimulating redox processes, enhancing glucose utilisation and improving regional blood flow in the cerebral tissues. The said effects result in the enhanced resistance of neurones to hypoxia.

Shortcoming of these agents is that they only stimulate the synthesis of neurotropic factors but do not possess any neurotropic activity in themselves (2). These agents are not free of side effects and contraindications. Inasmuch as potentialities for intracellular biosynthesis in altered neurones are not substantial the stimulation of regeneration by means of introducing natural neurotropic factors appears to be more expedient.

There is also known Cerebrolysin—a non-protein cerebral hydrolysate comprising free amino acids and low-molecular peptides (3). The said agent increases the efficacy of aerobic energy metabolism, improves intracellular protein synthesis, reveals neuroprotective and neurotropic activity and exerts a positive effect in case of cognitive alterations.

Shortcoming of the said agent is that its neurotropic effects are less potent than those of the natural neurotropic factors. The drug administration does not provide considerable restoration of the anatomical structure and functional activity in damaged cerebral and spinal neurones (4, 5, 6). Cerebrolysin application may entail side effects. Moreover, acute renal failure is a contraindication for the said agent.

There are known neurotropic factors that are low-molecular proteins (15–30 kDa) synthesised by the cell elements of the central nervous system: neurone growth factor, cerebral derivative neurotropic factor, 3-, 4- and 5-neurotrophins, basic and acid fibroblast growth factors, epidermal growth factor, astrocyte factor—S-100 protein, lipoprotein (7, 8). Introduction of the said agents in low doses into neurone cultures provides cell functioning, enables formation and growth of axons via stimulation of RNA, DNA, and protein biosynthesis. Neurotropic factors are necessary both for the survival and differentiation of neurones during embryogenesis and for the maintenance of morphologic and functional properties of mature cells. However, it has been proven in the studies that their efficacy is limited to only neuroprotective activity and the neurotropic effects are manifested at later stages. Endogenous peptide substances in the central nervous system are known to be signal transducers in interneurone or neuroeffector transmission and can function as neurohormones, neurotransmitters or neuromodulators (9, 10, 11). These endogenous substances, neuropeptides, are released from communicational neuronal elements so that a target structure recognises them as information. Neuropeptides have been found to be means of integral modulation of the CNS functions such as reparative processes, memory, motional activity, sensations of pain and pleasure, etc.

There are known peptides Cortexin and Epithalamin extracted from the cattle brain (molecular weight—10 kDa) and capable of supporting structural and functional homeostasis of cell populations secreting these peptides (12, 13).

The present application distinguishes itself from the prior art publications by a new amino sequence L-Ala-L-Glu-L-Asp-L-Pro and is created to solve the problem of obtaining new peptides with neurone functional stimulating activity.

DISCLOSING OF THE INVENTION

The present invention is aimed at obtaining a novel biologically active substance of peptide origin capable of stimulating the functional activity of neurones. The disclosed peptide compound, tetrapeptide, does not have any structural analogues.

In accordance with the invention, tetrapeptide L-alanyl-L-glutamyl-L-asparagyl-L-proline, L-Ala-L-Glu-L-Asp-L-Pro (SEQ ID NO:1), is disclosed.

In accordance with the invention, tetrapeptide L-alanyl-L-glutamyl-L-asparagyl-L-proline of the following amino acid sequence—L-Ala-L-Glu-L-Asp-L-Pro (SEQ ID NO:1)—reveals biological activity and, namely, stimulates the neuronal functional activity in the central and peripheral nervous systems due to the metabolic processes normalisation, stimulation of the antioxidation defence parameters, improvement in electrophysiological indices.

The tetrapeptide is obtained by a classical method of peptide synthesis in a solution (9).

The stimulating effect of L-Ala-L-Glu-L-Asp-L-Pro (SEQ ID NO:1) tetrapeptide on the functional activity of neurones was found in experiment. Biological activity was studied on the nervous tissue explants investigating the tetrapeptide tissue-specific effects, in rats exploring antioxidation defence indices and aerotonin metabolism in the brain and the cerebroprotective action in case of toxic and traumatic impacts.

In accordance with the invention, the pharmacological agent stimulating the neuronal functional activity contains as its active base an effective amount of the tetrapeptide of the general formula L-alanyl-L-glutamyl-L-asparagyl-L-proline (L-Ala-L-Glu-L-Asp-L-Pro (SEQ ID NO:1)) or its salts.

In accordance with the invention, the pharmacological agent stimulating the neuronal functional activity may contain salts of the amino group (acetate, hydrochloride, oxalate) or of the carboxyl groups (salts of metals—sodium, potassium, calcium, lithium, zinc, magnesium, and of other organic and inorganic cations such as ammonium and triethylammonium).

In accordance with the invention, the pharmacological agent is preferably designated for parenteral, intranasal or oral administration.

The applied pharmacological agent stimulating the neuronal functional activity is capable of restoring the metabolism and growth of altered nerve tissue structures.

In the applied invention, including examples of the preferred embodiments, the following terminology accepted in the art is used.

"Pharacological agent" in the present application refers to the utilisation of any drug form containing the tetrapeptide or its salts that can be applied in medicine for preventive and/or therapeutic purposes as an agent for restoring the structural and functional integrity of nerve tissue.

"Effective amount" in the present application refers to the utilisation of such an amount of the active base that, in accordance with quantitative indices of activity and toxicity thereof, as well as being on the available knowledge of the persons skilled in the art, must be effective in the given drug form.

"Pharmaceutical composition" in the present application refers to the utilisation of different drug forms of the medicinal agent.

To obtain pharmaceutical compositions comfortable with the present invention the applied tetrapeptide or the pharmaceutically applicable derivatives thereof preferably are to be mixed as an active ingredient with a pharmaceutical carrier in accordance with the methods for compounding accepted in pharmaceutics.

The carrier can be of different forms depending on the drug form of the agent desirable for administration to a body, for instance, parenteral, intranasal or oral.

To produce compositions in the preferred dose form for oral administration any known pharmaceutical components can be used.

For parenteral (intranasal) administration the carrier normally comprises sterile water, although other ingredients instrumental for stability or sterility can be included.

In accordance with the invention, the method implies preventive or therapeutic administration to the patient of the claimed pharmacological agent dosing from 0.01 to 100 µg/kg of the body weight, at least once a day for a period necessary for attaining a therapeutic effect—from 10 to 40 days with respect to the character and severity of a pathologic process.

In accordance with the invention, the tetrapeptide is active in case it is administered in doses from 0.01 to 100 µg/kg of the body weight though lower (higher) doses may be employed with respect to the character and severity of a pathologic process.

INDUSTRIAL APPLICATION

Figure 1:
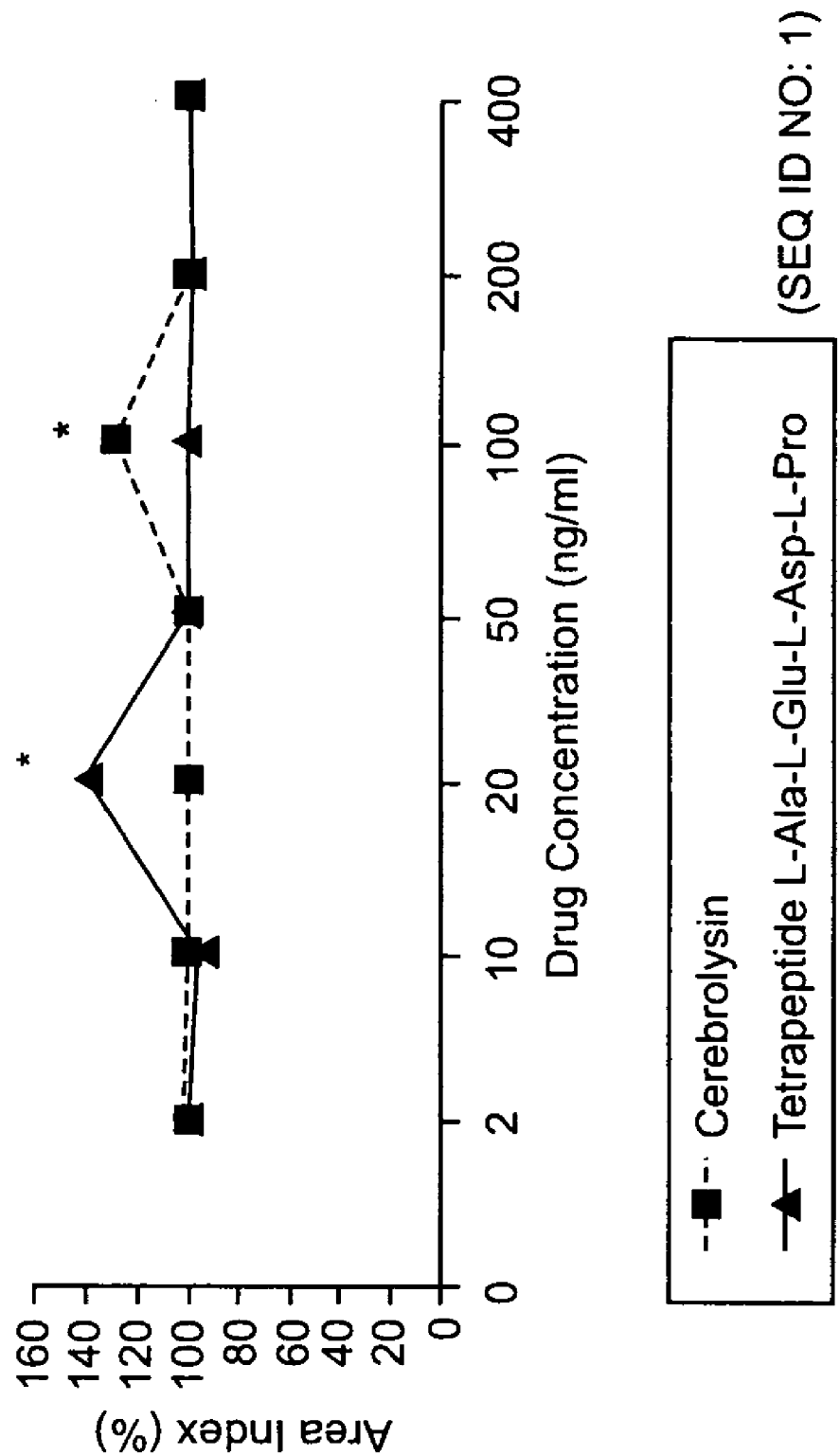
FIG. 1 is a graph plotting area index against drug concentration with curves shown for Cerebrolysin and Tetrapeptide L-Ala-L-Glu-L-Asp-L-Pro (SEQ ID NO: 1).

The invention is illustrated by an example of the synthesis of the tetrapeptide with the formula L-alanyl-L-glutamyl-L-asparagyl-L-proline (L-Ala-L-Glu-L-Asp-L-Pro (SEQ ID NO:1)) (Example 1), by the examples of tests for toxicity and biological activity of the tetrapeptide (Examples 2, 3, 4, 5, 6, 7, 8, 9) and also by examples on the results of the tetrapeptide clinical application demonstrating the pharmacological properties thereof and confirming the possibility to achieve a preventive and/or therapeutic effect (Examples 9 and 10).

Example 1

Synthesis of L-Ala-L-Glu-L-Asp-L-Pro Tetrapeptide

1. Product name: L-Alanyl-L-Glutamyl-L-Aspartyl-L-Proline.

2. Structural formula: H-Ala-Glu-Asp-Pro-OH.

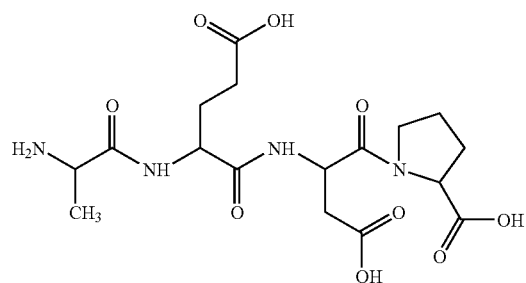

3. Gross formula without ion pair: $C_{17}H_{26}N_4O_9$.
4. Molecular weight without ion pair: 430.41.
5. Ion pair: acetate.
6. Appearance: white amorphous odourless powder.
7. Method of synthesis: the peptide is obtained by a classical method of synthesis in a solution in accordance with the following scheme.

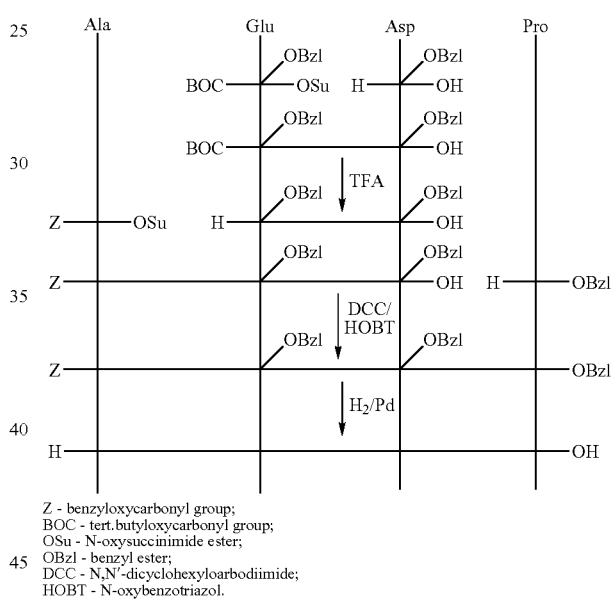

Z - benzyloxycarbonyl group;
BOC - tert.butyloxycarbonyl group;
OSu - N-oxysuccinimide ester;
OBzl - benzyl ester;
DCC - N,N'-dicyclohexyloarbodiimide;
HOBT - N-oxybenzotriazol.

N,N'-dimethylformamide was used as a solvent. By the introduction of aspartic acid the α-COOH group was protected by salification with triethylamine. The BOC-protecting group was unblocked with trifluoroacetic acid (TFA) solution, and the Z-protecting group was unblocked by means of catalytic hydrogenolysis. The product was extracted and purified by the method of preparative high-performance liquid chromatography (HPLC) on the column with a reversed phase.

Specification of the ready product:

| amino acid essay: | Glu | Asp | Ala | Pro |
|---|---|---|---|---|
|  | 1.10 | 1.01 | 1.00 | 1.10 | peptide content: 98.56% (by HPLC, 200 nm);
thin layer chromatography (TLC) – individual; $R_1$ = 0.67 (acetonitrile-acetic acid-water 5:1:3);
moisture content: 7%;
pH of 0.001% solution: 4.24;

-continued specific rotary power: $[\alpha]_D^{25}$: − 78.9° (c = 1.09, $H_2O$), "Polamat A", Carl Zeiss Jena.

Example of Synthesis:
1) BOC-Glu(OBzl)-Asp(OBzl)-OH (I), N-tert.butyloxycarbonyl-(γ-benzyl)glutamyl-(β-benzyl)aspartate 4.34 g (0.0100 mole) of N-oxysuccinimide ester of N-tert.butyloxycarbonyl-(γ-benzyl)glutamic acid BOC-Glu(OBzl)-OSu are dissolved in 20 ml of dimethylformamide and added 1.72 ml (0.0125 mole) triethylamide and 2.80 g (0.0125 mole) of β-benzylaspartate. The mixture is stirred within 24 hours at room temperature. The product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water and dried over anhydrous sodium sulphate. Ethyl acetate is filtered and removed in vacuo at 40° C. The residue is dried in vacuo over $P_2O_5$. As a result, 5.68 g (≈100%) of oil is obtained.

$R_f$=0.42 (benzene-acetone 2:1, Sorbfil plates, 8–12 μm of Silicagel, development—UV and chlorine/benzidine).

2) TFA H-Glu(OBzl)-Asp(OBzl)-OH (II), trifluoroacetate (γ-benzyl)-glutamyl-(β-benzyl)aspartate 5.68 g (≈0.01 mole) of N-tert.butyloxycarbonyl-(γ-benzyl)glutamyl-(β-benzyl)aspartate (I) are dissolved in 20 ml of dichloromethane-trifluoroacetic acid mixture (3:1). In 2 hours the solvent is removed in vacuo at 40° C., the removal is repeated with an addition of another portion of dichlormethane (2×10 ml) and the residue is dried in vacuo over NaOH, 5.80 g (≈100%) of oil is obtained. $R_f$=0.63 (n-butanol-pyridine-acetic acid-water, 15:10:3:12).

3) Z-Ala-Glu(OBzl)-Asp(OBzl)-OH (III), N-benzyloxycarbonyl alanyl-(γ-benzyl)glutamyl-(β-benzyl)aspartate 5.65 g (0.01 g) of trifluoroacetate of (γ-benzyl)glutamyl-(β-benzyl)aspartate (II) are dissolved in 10 ml of dimethylformamide, added 2.80 ml (0.02 mole) triethylamine and 4.14 g (0.013 mole) of N-oxysuccinimide ester of N-benzyloxycarbonyl alanine. The mixture is stirred within 24 hours at room temperature. The product is precipitated with 0.5N sulphuric acid solution (150 ml), extracted by ethyl acetate (3×30 ml), washed in 0.5N sulphuric acid solution (2×20 ml), water, 5% sodium bicarbonate solution (1×20 ml), water, 0.5N sulphuric acid solution (2×20 ml), water and dried over anhydrous sodium sulphate. Ethyl acetate is filtered, removed in vacuo at 40° C. and the residue is crystallised in the ethyl acetate/hexane system. The product is filtered and dried in vacuo over $P_2O_5$. The yield is 4.10 g (66%). Melting point—154° C. $R_f$=0.48 (benzene-acetone, 1:1), $R_f$=0.72 (n-butanol-pyridine-acetic acid-water, 15:10:3:12).

4) Z-Ala-Glu(OBzl)-Asp(OBzl)-Pro-OH(III), benzyl ether of N-benzyloxycarbonyl alanyl-(γ-benzyl)glutamyl-(β-benzyl)aspartylproline 0.72 g (3 mmole) of HCl H-Pro-OBzl, proline benzyl ester hydrochloride is suspended in 15 ml of tetrahydrofuran and added 0.4 ml (3 mmole) of triethylamine while stirring; subsequently in 5 minutes 1.28 g (2 mmole) of N-benzyloxycarbonyl alanyl-(γ-benzyl)glutamyl-(β-benzyl)aspartate (III) and 0.27 g (2 mmole) of N-oxybenzotriazole are added. The mixture is cooled down to 0° C. Afterwards, solution of 0.42 g (2 mmole) of the N,N'-dicyclohexylcarbodiimide in 5 ml of tetrahydrofuran cooled down to 0° C. is added. The mixture is stirred at 0° C. for 2 hours and left to stir for a night at room temperature. The residue of dicyclohexylurea is filtered out, the solvent is removed in vacuo and the residue is dissolved in 30 ml of ethyl acetate. The solution is washed in 1N hydrochloric acid solution, water, 5% sodium bicarbonate solution, water, 1N hydrochloric acid solution, water and dried over anhydrous sodium sulphate. The solvent is removed in vacuo and crystallised in the ethyl acetate/hexane system. The yield is 1.50 g (90%). $T_{ml}$=125–128° C. $R_f$=0.40 (benzene-acetone, 2:1).

5) H-Ala-Glu-Asp-Pro-OH (IV), alanyl-glutamyl-aspartyl-proline 1.50 g of N-benzyloxycarbonyl alanyl-(γ-benzyl)glutamyl-(γ-benzyl)aspartylproline of benzyl ester(III) is hydrogenated in the methanol-water-acetic acid system (3:1:1) over Pd/C catalyst. The progress of unblocking is monitored by TLC method in the benzene-acetone (2:1) and acetonitrile-acetic acid-water (5:1:3) systems. After the reaction completion the catalyst is filtered out, the filtrate is removed in vacuo and the residue is crystallised in the water/methanol system. The product is dried in vacuo over KOH. The yield is 0.66 g (86%). $R_f$=0.67 (acetonitrile-acetic acid-water, 5:1:3).

For purification, 508 mg of the product is dissolved in 4 ml of 0.01% trifluoroacetic acid (sample pH—2.23) and subject to HPLC on a column with a reversed phase 50×250 mm Diasorb-130-C16T, 7μ. The chromatograph used is Beckman System Gold, 126 Solvent Module, 168 Diode Array Detector Module. Chromatography conditions A: 0.1% TFA; B: 50% MeCN/0.1% TFA, gradient B 0→16% in 240 min. Sample volume equals 5 ml, detection is conducted by 215 nm, scanning—by 190–600 nm, flow rate is 10 ml/min. The fraction is selected within 127–155 min. The solvent is removed in vacuo at the temperature not exceeding 40° C. The removal is repeated 5 times with 10 ml of 10% acetic acid solution. Finally the residue is dissolved in 20 ml of deionised water and lyophilised. As a result, 303 mg of the purified product is obtained in the form of amorphous odourless white powder.

In order to obtain corresponding salts of carboxyl groups, the free tetrapeptide is added a calculated amount of the water solution of a corresponding metal hydroxide (NaOH, KOH, $ZnOH_2$, LiOH, $CaOH_2$, $MgOH_2$, $NH_4OH$). To obtain triethylammonium salt the processing is performed similarly using triethylamine as a base.

6) Ready product analysis

Peptide content is defined by HPLC method on the Supelco LC-18-DB column, 4.6×250 mm, grad. LC-18-DB. A: 0.1% TFA; B: 50% MeCN/0.1% TFA; gradient B 0→20% in 30 min. Flow rate is 10 ml/min. Detection by 220 nm, scanning—by 190–600 nm, sample volume equals 20 μl. Peptide content—98.56%.

Amino acid assay is carried out on the tester AAA "T-339" Prague. Hydrolysis is conducted in 6N HCl at 125° C. within 24 hours.

| Glu | Asp | Ala | Pro |
|-----|-----|-----|-----|
| 1.10 | 1.01 | 1.00 | 1.10 |

TLC: individual, $R_f$=0.67 (acetonitrile-acetic acid-water, 5:1:3, Sorbfil plates, 8–12 μm of Silicagel, development in chlorine/benzidine).

Moisture content: 7% (gravimetrically according to the mass loss by drying,—20 mg at 100° C.).

pH of 0.001% solution: 4.24 (potentiometrically).
Specific rotary power: $[\alpha]_D^{25}$: −78.9° (c=1.09, H$_2$O), "Polamat A", Carl Zeiss Jena.

Example 2

Study of L-Ala-L-Glu-L-Asp-L-Pro Tetrapeptide for Toxicity

Possible toxic effects of L-Ala-L-Glu-L-Asp-L-Pro (SEQ ID NO:1) tetrapeptide on the organism were studied in compliance with "The rules of preclinical estimation of safety of pharacological agents" (GLP) approved by the Department of State Control on Medicinal Agents and Medical Equipment of the Russian Federation of Dec. 29, 1997.

Objective of the study consisted in defining the tolerable toxic drug doses of the agent, estimating the stage and character of pathologic alterations in various organs and systems and in exploring the correlation between the toxic effects and the dose and duration of the drug application.

Acute toxicity of L-Ala-L-Glu-L-Asp-L-Pro (SEQ ID NO:1) tetrapeptide was determined according to Kerber. The study was performed on 66 white unbred male mice weighing 20 to 23 g kept in vivarium under standard regimen and fed upon standard rations. The animals were randomly divided into 6 equal groups by 11 mice in each. The animals were subject to a single intramuscular administration of 0.25 ml of the preparation in doses 1 mg/kg, 2 mg/kg, 3 mg/kg, 4 mg/kg, 5 mg/kg (several thousand times exceeding the therapeutic dose recommended for clinical trials). The control animals were administered the similar amount of saline.

Within 72 hours and later on in 14 days none of the mice in either of the groups died. No alterations in the general state, behaviour, motional activity, hair and skin integument, physiologic discharges of the animals were registered.

Thus, L-Ala-L-Glu-L-Asp-L-Pro (SEQ ID NO:1) tetrapeptide in doses several thousand times exceeding the therapeutic one, recommended for clinical study, did not induce any acute toxic reactions, which indicated a wide therapeutic applicability of the preparation.

Subacute toxicity of L-Ala-L-Glu-L-Asp-L-Pro (SEQ ID NO:1) tetrapeptide was studied on 60 white unbred rats weighing 150 to 250 g. The experimental animals were administered the preparation intramuscularly once a day, daily for 90 days in doses 1 µg/kg, 0.3 mg/kg, 3 mg/kg in 0.5 ml of saline. The control animals were administered the similar amount of saline.

Within the entire period of study the animals were under daily supervision. Animals' behaviour, food and water consumption, the state of their hair integument and mucous membranes were registered. The animals were weighed once a week. Prior to and on the 30$^{th}$, 60$^{th}$ and 90$^{th}$ days of the drug administration, the morphologic composition and properties of the peripheral blood in the animals were examined. Upon the study completion, biochemical and coagulologic blood indices were explored.

Chronic toxicity of L-Ala-L-Glu-L-Asp-L-Pro (SEQ ID NO:1) tetrapeptide obtained by the claimed method was investigated by means of a long-term administration thereof to rats weighing 150–250 g. The animals were subject to daily intramuscular administration of the drug in doses 1 µg/kg, 0.1 mg/kg, 1 mg/kg in 0.5 ml of saline for 6 months. Animals' behaviour, food and water consumption, the state of hair integument and mucous membranes were registered. The animals were weighed daily for the first 3 months of the experiment and then—once a month. Haematological and biochemical investigations were conducted in 3 months after the onset of the drug administration and on the experiment completion. Functions of the cardiovascular system, liver, pancreas, kidneys and adrenal glands were assessed. After the treatment completion some animals were subject to pathomorphologic examination with the purpose to estimate the state of different sections of the brain and bone marrow, heart, aorta, lungs, liver, kidneys, endocrine and immune organs.

Assessment of the general state of the animals, morphologic and biochemical indices of the peripheral blood, morphologic state of the intrinsic organs, state of the cardiovascular and respiratory systems, liver and kidney functions revealed no pathologic alterations.

Study of L-Ala-L-Glu-L-Asp-L-Pro (SEQ ID NO:1) tetrapeptide for subacute and chronic toxicity indicated the absence of any side effects in case of prolonged drug administration in doses which 100 to 1000 times exceeded the therapeutic one.

Example 3

Effect of L-Ala-L-Glu-L-Asp-L-Pro Tetrapeptide on the Development of Cerebral Cortex Explants The experiments were carried out on 73 cerebral cortex fragments of 10–11 day old chicken embryos. Culture medium for the explants comprised 35% Eagle's solution, 25% foetal calf serum, 35% Henks' solution, 5% chicken embryonic extract. The medium was also added glucose (0.6%), insulin (0.5 IU/ml), penicillin (100 IU/ml), glutamine (2 mM). The cerebral cortex fragments were placed in the said medium and cultivated in Petri dishes in a thermostat at 36.7° C. for 2 days. L-Ala-L-Glu-L-Asp-L-Pro (SEQ ID NO:1) tetrapeptide and Cerebrolysin in concentrations 0.5, 1, 2, 20, 50, 100, 200, 400, 800, 1000 ng/ml were added into the experimental medium. Area index (AI) served as a criterion of biological activity and reflected the ratio of the entire explant area including the growth zone to the initial area of the cortex fragment. Student's t-criterion was applied to assess the significance of differences between the compared mean AI values. AI values were expressed percent. The control AI value was taken for 100%.

The growth zone of the control cortex explants included short axons, neuroglia cells migrating to the periphery and fibroblast-like cells.

Following series of experiments were performed to study the direct effect of the drugs on the cerebral cortex fragments.

Cerebrolysin in various concentrations was added to the culture medium of the cerebral cortex explants of the chicken embryos. On the 3$^{rd}$ day of cultivation there was registered a significant increase in the explant AI (by 30±2%) in the concentration of 100 ng/ml in comparison with the control AI values. No significant AI values of the cortex explants in case of applying other concentrations of Cerebrolysin were observed (FIG. 1). The development of cerebral explants was notably stimulated by L-Ala-L-Glu-L-Asp-L-Pro (SEQ ID NO:1) tetrapeptide in concentration 20 ng/ml. Thereby, AI of the experimental explants was higher by 40±7% as compared to AI of the control cerebral cortex fragments.

The same axon-stimulating effects by the same concentrations were revealed in case of prolonged (for 7 days) cultivation of the cortex explants. Occasionally a statistically insignificant decrease in the explant AI was observed, presumably due to the retraction of nerve fibres in case of prolonged cultivation.

Thus, with respect to the cerebral tissues there was registered a decreased threshold of the effective concentrations for L-Ala-L-Glu-L-Asp-L-Pro (SEQ ID NO:1) tetrapeptide in comparison with that for Cerebrolysin. For instance, Cerebrolysin stimulated cultivated cortical fragments in concentration 100 ng/ml, while the tetrapeptide—in concentration 20 ng/ml, which indicated a more marked and targeted action of L-Ala-L-Glu-L-Asp-L-Pro (SEQ ID NO:1) tetrapeptide on the cerebral cortex neurones.

Example 4

Effect of L-Ala-L-Glu-L-Asp-L-Pro Tetrapeptide on the Intensity of Lipid Peroxide Oxidation Reactions in the Cerebral Cortex The intensity of lipid peroxide oxidation (LPO) was assessed by the content of initial LPO products—diene conjugates and end products—Schiff bases. The degree of protein peroxidation was estimated by the content of carbonyl-derived amino acids in proteins after their interaction with 2,4-dinitrophenylhydrazine.

The study was conducted on 20 white unbred rats. 1 μg of the tetrapeptide was administered to the animals intraperitoneally daily for 5 days.

The tested tetrapeptide was found to significantly suppress the formation of LPO products in the cerebral cortex. Under the tetrapeptide effect the content of diene conjugates diminished significantly and Schiff bases tended to decrease as well. Moreover, the tetrapeptide application inhibited protein peroxidation as well as LPO (Table 1).

TABLE 1

Effect of L-Ala-L-Glu-L-Asp-L-Pro tetrapeptide on the intensity of lipid peroxide oxidation reactions in the cerebral cortex of rats

| Indices | Groups of animals | |
| --- | --- | --- |
|  | Control | L-Ala-L-Glu-L-Asp-L-Pro tetrapeptide |
| Diene conjugates (nmole/g of the tissue) | 40.19 ± 2.55 | 29.67 ± 1.93* |
| Schiff bases (IU/g of the tissue) | 318.0 ± 28.9 | 245.2 ± 23.9 |
| Degree of protein peroxidation (μmole/mg of protein) | 7.53 ± 0.40 | 4.81 ± 0.09* |

*P < 0.01 in comparison with the control.

The obtained data indicated that the application of L-Ala-L-Glu-L-Asp-L-Pro (SEQ ID NO:1) tetrapeptide suppressed the formation of the lipid peroxide oxidation products and protein peroxidation in the cerebral cortex.

Example 5

Effect of L-Ala-L-Glu-L-Asp-L-Pro Tetrapeptide on the Toxic Effects of Neurotropic Agents Investigated was the action of L-Ala-L-Glu-L-Asp-L-Pro tetrapeptide on the toxic effects of neurotropic agents of various pharmacological groups.

In an hour after an intramuscular injection of saline (control) or L-Ala-L-Glu-L-Asp-L-Pro tetrapeptide (5 μg/kg) the rats were intraperitoneally administered toxic doses of different neuropharmacological agents (apomorphine, haloperidol, nicotine and caffeine). Thereby, the parameters of vertical (anxiety) and horizontal (locomotor activity) spontaneous motional activity were registered.

Apomorphine exerts an emetic effect due to the stimulation of chemoreceptive triggering zone in the medulla oblongata. Moreover, apomorphine is capable of interacting with dopamine receptors and of stimulating the dopaminergic structures of the brain. In the experiments, hyperlocomotor activity, hyperthermia, "psychosis" and myotonia were observed. L-Ala-L-Glu-L-Asp-L-Pro tetrapeptide counteracted apomorphine (diminished anxiety and locomotor activity).

Haloperidol refers to neuroleptics and reveals a low adrenolytic activity. In the experiments the said agent caused hypothermia, catalepsy, "depression", myoplegia and a decrease in locomotor activity. L-Ala-L-Glu-L-Asp-L-Pro tetrapeptide acted as a pharmacological antagonist of haloperidol (increased anxiety and locomotor activity).

Nicotine possesses an n-cholinomimetic activity. In the experiments the said agent enhanced vertical and horizontal motional activity as well as muscular tonus. L-Ala-L-Glu-L-Asp-L-Pro tetrapeptide decreased the influence of nicotine on the animals' anxiety.

Caffeine is a psychostimulator. The mechanism of its action is based on the suppression of phosphodiesterase activity and a therewith-associated increase in cAMP content. In the experiments caffeine caused hyperlocomor activity and fostered zoosocial contacts in the animals. L-Ala-L-Glu-L-Asp-L-Pro tetrapeptide lowered caffeine-induced anxiety but did not affect locomotor activity.

The property of L-Ala-L-Glu-L-Asp-L-Pro tetrapeptide to suppress the toxic effects of such agents as adrenostimulators, neuroleptics, cholinomimetics and psychostimulators can be employed in the treatment for neurotropic poisoning.

Example 6

Effect of L-Ala-L-Glu-L-Asp-L-Pro Tetrapeptide on Serotonin Metabolism

The study was conducted on the model of electrically induced pain stress.

L-Ala-L-Glu-L-Asp-L-Pro tetrapeptide was administered to the rats in dose 5 μg/kg immediately before or right after the impact of electrically induced pain stress. In an hour the content of serotonin and its metabolite, 5-oxyindoleacetic acid, was measured in the parietal and posterior frontal regions of the brain.

In case of emotionally induced pain stress both the synthesis and decay of serotonin were stimulated by means of the subsequent fast depletion of these processes. Compensatory in character, the stimulation of serotonin metabolism diminishes the emotional perception of a pain impact, Natural "drawback" of the said mechanism consists in a quick transition to the state of decompensation. In control (untreated stress) the level of serotonin lowered, while that of 5-oxyindoleacetic acid rose (metabolic depletion phase).

Post-stress introduction of L-Ala-L-Glu-L-Asp-L-Pro tetrapeptide increased the content of serotonin and diminished the content of 5-oxyindoleacetic acid in the brain. Pre-stress administration of L-Ala-L-Glu-L-Asp-L-Pro tetrapeptide promoted similar effects, which, however, were insignificant. L-Ala-L-Glu-L-Asp-L-Pro tetrapeptide did not induce any changes in the levels of serotonin and its metabolite in the intact animals.

Thus, introduction of L-Ala-L-Glu-L-Asp-L-Pro tetrapeptide immediately after a electrically induced pain stress normalised the content of serotonin and its metabolite, 5-oxyindoleacetic acid, in the brain.

Example 7

Effect of L-Ala-L-Glu-L-Asp-L-Pro Tetrapeptide on the Indices of Memory and Learning in Case of Amnestic Impacts of Electroconvulsive Shock and Ethanol Intoxication Nootropic activity of L-Ala-L-Glu-L-Asp-L-Pro tetrapeptide was studied with the application of the conditioned reflex of passive avoidance (CRPA) in the intact animals and under the conditions of amnestic impacts (electroconvulsive treatment and ethanol intoxication).

The experiments were carried out on male mice weighing 20 to 24 g. For each animal the period of stay in dark and lighted chamber departments was registered during 2 min. before the training. Only the animals, whose stay period in the lighted department did not exceed 40 sec., were included into the experimental group. The animals were trained by means of applying an electric pain stimulus in the preferred dark department, which lasted until the animal left this department. L-Ala-L-Glu-L-Asp-L-Pro tetrapeptide was introduced intraperitoneally 60 min. before the training. Testing was performed in 2 and 24 hours after the training. The period the animal stayed in the dark and lighted chamber departments and the number of animals not entering the dark department ("educated" animals) were recorded.

Electroconvulsive shock (ECS) was induced in the mice no later than in 10 sec. after the training via corneal electrodes by an electric impulse of 25 mA, which lasted for 0.5 sec. L-Ala-L-Glu-L-Asp-L-Pro tetrapeptide was introduced intraperitoneally 60 min. before the training. Testing was performed in 24 hours after the training.

Ethanol was administered to the mice orally for 13 days in the form of a 10% solution. Training was held twice: on the 14$^{th}$ day of ethanol administration and in 24 hours after the first training. L-Ala-L-Glu-L-Asp-L-Pro tetrapeptide was administered intraperitoneally 30 min. before the training. Testing was performed in 2 and 24 hours after the first and second training sessions. Results of the study are displayed in Tables 2–4.

TABLE 2

Effect of L-Ala-L-Glu-L-Asp-L-Pro tetrapeptide on the formation of CRPA in the intact white mice

| Agent | Number of animals | Trained animals (%) 2 hours | Trained animals (%) 24 hours | Total period of stay in the dark chamber during 2 min. (sec.) 2 hours | Total period of stay in the dark chamber during 2 min. (sec.) 24 hours |
|---|---|---|---|---|---|
| Control | 22 | 77 | 59 | 17.2 ± 5.8 | 19.7 ± 5.8 |
| L-Ala-L-Glu-L-Asp-L-Pro tetrapeptide | 22 | 86 | 68 | 11.4 ± 5.2 | 26.6 ± 5.9 |

TABLE 3

Effect of L-Ala-L-Glu-L-Asp-L-Pro tetrapeptide on the formation of CRPA in the mice subject to ECS-induced amnestic impact

| Agent | Number of animals | Trained animals (%) | Total period of stay in the dark chamber in 24 hours |
|---|---|---|---|
| Control | 53 | 14 | 62.3 ± 4.2 |
| Tetrapeptide L-Ala-L-Glu-L-Asp-L-Pro | 48 | 25 | 38.1 ± 4.4* |

*$P < 0.001$ in comparison with the control indices.

TABLE 4

Effect of L-Ala-L-Glu-L-Asp-L-Pro tetrapeptide on the formation of CRPA in the mice subject to ethanol-induced amnestic impact

| Group | Trained animals (%) 1 | 2 | 3 | 4 | Total period of stay in the dark chamber (sec.) 1 | 2 | 3 | 4 |
|---|---|---|---|---|---|---|---|---|
| Control | 0 | 13 | 56 | 82 | 70.4 ± 6.0 | 53.2 ± 5.7 | 24.7 ± 4.2 | 9.6 ± 6.5 |
| L-Ala-L-Glu-L-Asp-L-Pro tetrapeptide | 13 | 31 | 77 | 86 | 47.8 ± 5.7* | 41.6 ± 5.8 | 13.7 ± 5.7 | 7.6 ± 5.7 |

*$P < 0.01$ comparing to the control indices.
Note:
1-in 2 hours after the training;
2-in 24 hours after the training;
3-in 2 hours after the repeated training;
4-in 24 hours after the repeated training.

The obtained data demonstrate that L-Ala-L-Glu-L-Asp-L-Pro tetrapeptide does not influence the formation of CRPA in the intact animals. However, the agent improves the indices of memory and learning in case of amnestic impacts,

Example 8

Effect of L-Ala-L-Glu-L-Asp-L-Pro Tetrapeptide on Repair Processes in the Brain after a Craniocerebral Injury Effect of L-Ala-L-Glu-L-Asp-L-Pro tetrapeptide on repair processes in the brain was assessed on the model of acute severe craniocerebral injury. Dynamics of the CNS functional restoration was defined by the tests on the coordination of movements and muscular tonus of the animals as well as on their abilities for learning and reproduction of conditioned reflex skills.

Severe craniocerebral compression in the rats was caused by a falling lead weight. In 1, 12, 48 and 96 hours the experimental animals were intramuscularly injected with L-Ala-L-Glu-L-Asp-L-Pro tetrapeptide. Animals in the $2^{nd}$ group received Cerebrolysin.

Abilities for learning and skill reproduction were estimated by the test on the conditioned reflex of active avoidance (CRAA). To estimate the muscular tonus and coordination of movements the rats were rotated on a pivot at an increasing speed. Simultaneously, the retention time was measured.

In 48 hours all the survived animals lost their ability for training. In 96 hours the number of trainable animals among the rats treated with L-Ala-L-Glu-L-Asp-L-Pro tetrapeptide was twice as much as that in the controls. In 30 days the indices of learning in the tetrapeptide-injected rats were also higher than those in control.

The severe craniocerebral injury entailed a pronounced asthenoneurotic syndrome in the animals, decreased their coordination and muscular tonus. Test by the method of "rotating pivot" demonstrated that L-Ala-L-Glu-L-Asp-L-Pro tetrapeptide facilitated the restoration of movement coordination and muscular tonus in 48 hours after the trauma (the time of retention on the pivot twice exceeded that in control).

In case of severe craniocerebral compression Cerebrolysin was less effective than L-Ala-L-Glu-L-Asp-L-Pro tetrapeptide.

Thus, application of the studied agent significantly improved the abilities of the animals for learning and conditioned reflex skills reproduction and also restored the coordination of movements and muscular tonus thereof. Favourable effect of the drug was observed already on the $4^{th}$ day after the trauma. By the $13^{th}$ day the indices of learning approached the normal values.

In case of acute severe craniocerebral injury the populations of neurones in the grey substance of the brain get damaged and destructed. Accelerated restoration of the CNS functions in the early posttraumatic period due to the effect of L-Ala-L-Glu-L-Asp-L-Pro tetrapeptide evidenced that the present tetrapeptide stimulated reparative processes in the brain.

which indicates the nootropic activity of the tested agent and its capacity to suppress the amnestic effects of ECS and ethanol.

Example 9

Effect of L-Ala-L-Glu-L-Asp-L-Pro Tetrapeptide on the Regeneration of the Compressed Peripheral Nerve The study was accomplished on 22 white unbred male mice weighing 25 to 30 g (7 experimental and 15 control animals).

At the $1^{st}$ stage of the study, the mice were chronically operated on to compress the fibular nerve. The fibular nerve (n. peroneus communus) in the Nembutal-narcotised mice (60 mg/kg, intraperitoneally) was compressed at a distance of 8 to 9 mm from the innervated muscle—long digital extensor (m. extensor digitorum longus—EDL). The animals were operated on the left hind leg, whilst the corresponding nerve and muscle of the right leg were intact and used further as an intact control.

Afterwards, since the $3^{rd}$ day after the nerve compression, the mice were intraperitoneally injected with L-Ala-L-Glu-L-Asp-L-Pro tetrapeptide in dose 10 μg/kg, daily for 8 days. The control mice were treated with an equivalent amount of saline.

On the $11^{th}$ day after the nerve compression surgery (and within 24 hours after the last tetrapeptide injection), the Nembutal-narcotised mice (60 mg/kg) were subject in vivo to electrophysiological tests for different functional parameters of the already germinated nerve and reinnervated skeletal muscular fibres (EDL).

Figure 2:
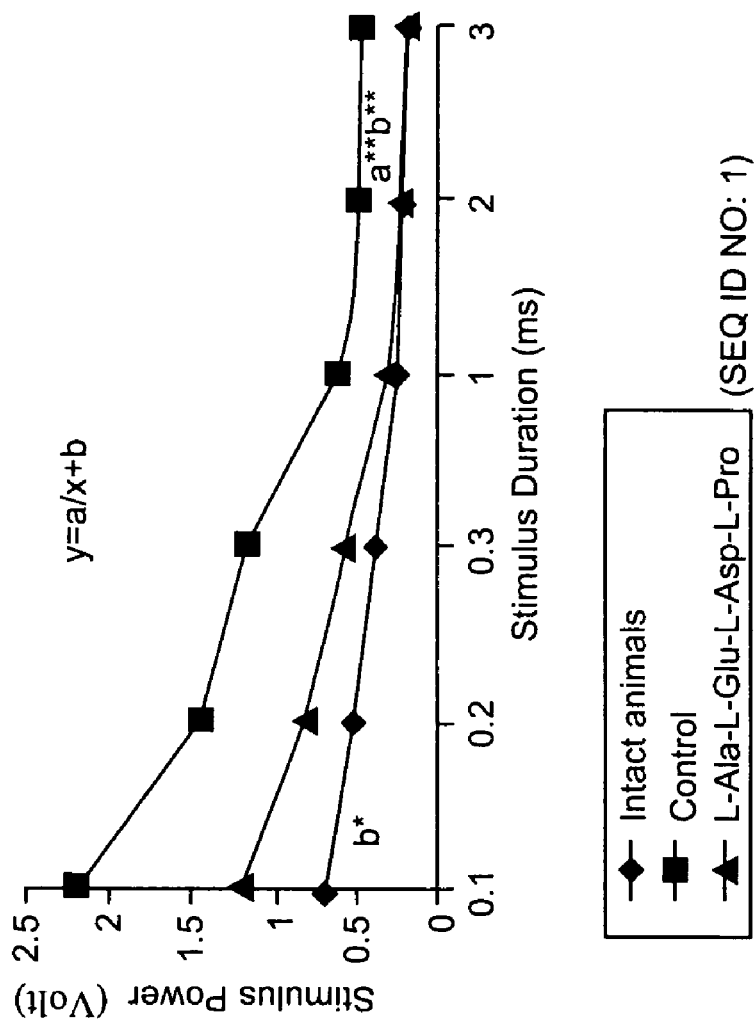
FIG. 2 is a graph plotting stimulus power versus stimulus duration with curves shown for Intact animals, Control, and L-Ala-L-Glu-L-Asp-L-Pro (SEQ ID NO: 1).

The obtained data indicated that in the experimental animals L-Ala-L-Glu-L-Asp-L-Pro tetrapeptide boosted the restoration of excitability threshold and promoted corresponding changes in the "strength-duration" curve for the regenerating neuromuscular system by the $11^{th}$ day after the nerve compression (FIG. 2). The FIG. 2 shows the effect of L-Ala-L-Glu-L-Asp-L-Pro tetrapeptide on the strength-duration curve of the stimuli applied to the nerve trunk. Note:
- a—coefficient for the curve form (hyperbola);
- b—coefficient for the strength-duration curve shift along the Y-axis;
- a and b parameters designate the features of the nerve electric excitability and the excitability threshold thereof.

This means that introduction of L-Ala-L-Glu-L-Asp-L-Pro tetrapeptide significantly and considerably (by 30–50%) improves one of the principal functional indices of the regenerating nerve—the electric threshold thereof, thus, accelerating the time of its restoration to the normal values.

Latent period of M-response was found to be another index significantly changed in the peripheral "nerve-muscle" system after the tetrapeptide introduction. The muscle M-response is a summarised electric reaction (total potential of the muscle action) recorded in response to the irritation of the motional nerve. It must be emphasised that shortening of the latent M-response period was more pronounced in the intact neuromuscular system (by 89%) comparing to the regenerating nerve (and the muscle) (by 59%). The latent M-response period is an integral parameter indicating the excitement conduction rate via axons, their fine intramuscular branches as well as synaptic transmission rate in the peripheral motor synapses. Since effect of the tetrapeptide L-Ala-L-Glu-L-Asp-L-Pro on the latent period of the M-response was more considerable in the intact nerve and muscle, this particular feature of the tetrapeptide activity appeared not to be directly associated with neuro- and myoregenerative processes but rather to indicate ability of the present agent to influence peripheral excitable structures (neural fibres, terminal sites, synapses, etc.) and to boost excitement transmission in peripheral neuromuscular system.

Figure 3:
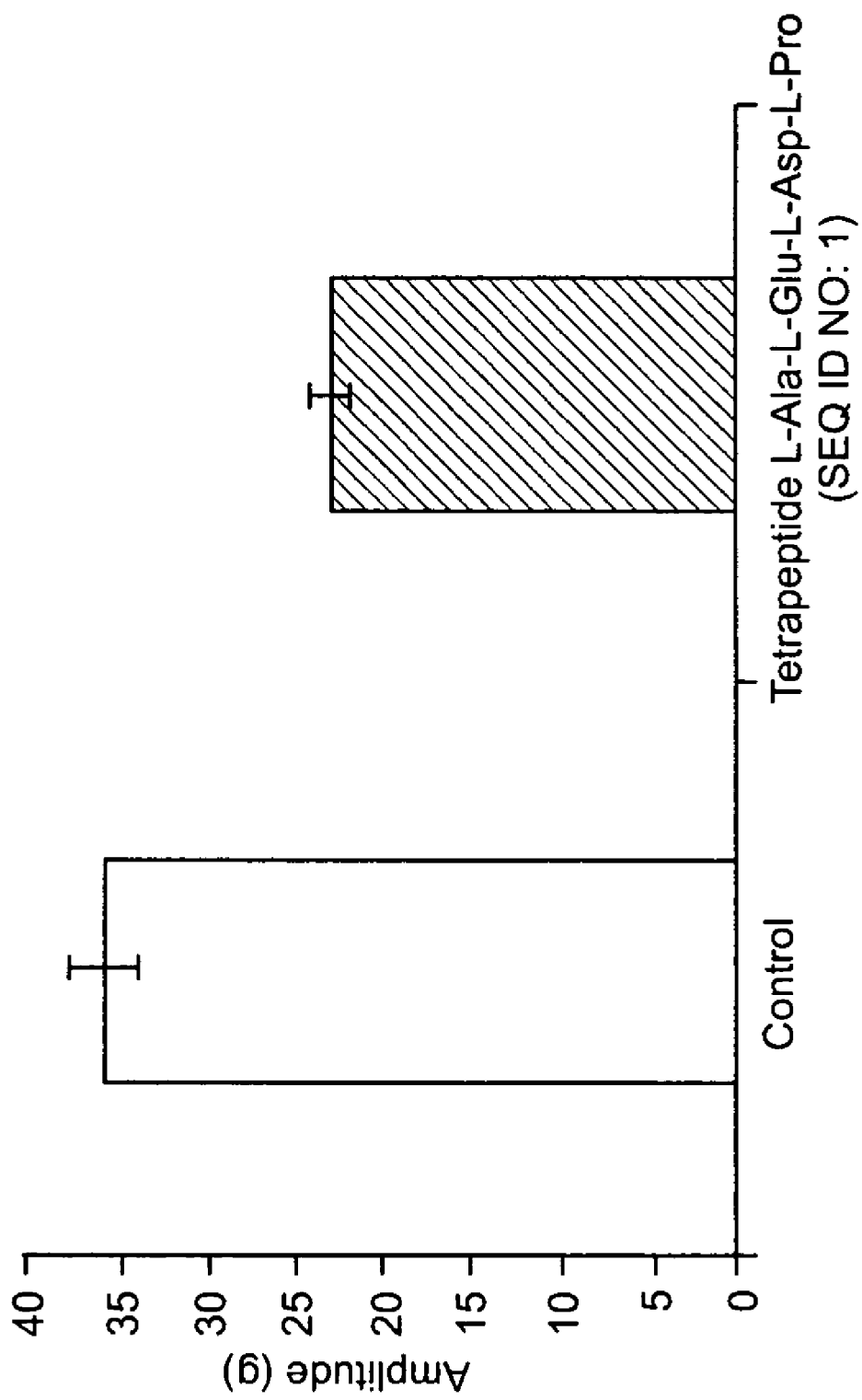
FIG. 3 is a bar graph plotting amplitude for control and tetrapeptide L-Ala-L-Glu-L-Asp-L-Pro (SEQ ID NO: 1).

Along with introduction of L-Ala-L-Glu-L-Asp-L-Pro tetrapeptide in the mice, there was found a tendency to diminish acetyl choline muscular contraction rate (FIG. 3) caused by the residual non-synaptic choline-reception preserved after the denervation on the surface of the muscular fibres. The acetyl choline muscular contraction is known to be mediated with non-synaptic choline reception that, in its turn, is a classic index for manifestation degree of neurotropic influence on the muscle, chiefly, from motoneurones. Thereby, a tendency to significantly suppress the acetyl choline muscular contraction against the background of the tetrapeptide introduction may be regarded as a result of neurotropic motoneurone influence on the choline reception of muscular fibres enhanced by the present agent or as an indication of direct neurotropic effects of the tetrapeptide itself on muscular fibres imitating neurotropic motoneurone activity.

Application of L-Ala-L-Glu-L-Asp-L-Pro tetrapeptide accelerated the restoration of various important functional indices in the nerve regenerating after compression. At that, the tetrapeptide stimulated regeneration both in the nerve and in the muscle and approximating them to the state characteristic for intact "healthy" motional units.

Thus, after the performed experiments L-Ala-L-Glu-L-Asp-L-Pro tetrapeptide was found to be non-toxic, able to stimulate activity of the cerebral neurones manifested in a marked cerebroprotective action, metabolic activation and high neurotropic activity.

The properties of L-Ala-L-Glu-L-Asp-L-Pro tetrapeptide found in the experimental preclinical studies allowed recommend it for the therapeutic and preventive application in various cerebral disorders. List of the disorders and their codes are given below in compliance with the International Classification of Diseases 1CD-9-CM (14).

In one embodiment of the invention, L-Ala-L-Glu-L-Asp-L-Pro tetrapeptide can be employed as a drug stimulating cerebral reparative processes and revealing cerebroprotective activity, as an agent for:
    treatment and prevention of trauma-associated cerebral lesions (800–959) including: treatment for cerebral lesions after a fracture of the cranial vault (1500), skull base (801), multiple bone fractures (804);
    treatment for the cerebral lesions in cases of intracranial trauma (850–854) (posttraumatic cerebral concussion (850), cerebral wounds and contusion (851), subarachnoid, subdural and extradural haemorrhage (852));
    treatment and prevention of traumatic shock (958.4);
    treatment for the cerebral lesions associated with the impact of radiation (990), lowered temperature (991), heat and light (992), air pressure (993), electric and ultrahigh frequency current;
    treatment and prevention of delayed-onset effects of skull fractures (905.0);
    treatment and prevention of delayed-onset effects of intracranial trauma (907.0);
    treatment and prevention of delayed-onset cerebral lesions induced by radiation (909.2), complications after surgical and other medical interventions (909.3).

In another embodiment of the invention, L-Ala-L-Glu-L-Asp-L-Pro tetrapeptide as a drug suppressing toxic effects of the neurotropic agents, stimulating cerebral repair processes and revealing cerebroprotective activity is used as an agent for the treatment and prevention of cerebral lesions after poisoning (960–999) including:
    treatment for the cerebral lesions after poisoning with therapeutic agents, medicinal and biological compounds (960–979);
    treatment for the cerebral impairment with agents of non-medical origin (980–989);
    treatment and prevention of delayed-onset cerebral lesions induced by poisoning with drugs (909.0) and non-medical substances (909.1).

In another embodiment of the invention, L-Ala-L-Glu-L-Asp-L-Pro tetrapeptide as a drug stimulating cerebral repair processes with nootropic activity is used as an agent for treatment and prevention of cerebral degenerative disorders (330–337) including:
    treatment and prevention of pediatric cerebral degenerative disorders (330);
    treatment and prevention of Alzheimer's disease (331.0), Pick's disease (331.1), senile cerebral degeneration (331.2) and hydrocephalus (331.3–331.4);
    treatment and prevention of Parkinson's disease (332) and other extra pyramidal disorders (333) (degenerative diseases of basal ganglia (333.0), essential tremor (333.1), myoclonus (333.2), tics of organic origin (333.3), Huntington's (hereditary) chorea (333.4) and other types of chorea, torsion dystonia (333.6–333.8));
    treatment and prevention of spinal-cerebellum disorders (Friedrich's ataxia (334.0), hereditary spastic paraplegia (334.1) and cerebellum ataxia in other disorders (334.4)).

In another embodiment of the invention, L-Ala-L-Glu-L-Asp-L-Pro tetrapeptide as a drug with nootropic activity, stimulating cerebral repair processes is used as an agent for treatment and prevention of senile and presenile organic psychotic disorders (290) including:
    treatment and prevention of senile dementia (290.1) including that concomitant to Alzheimer's disease (331.0), Jacob-Creutzfeldt disease (046.0) and Pick's disease (331.1);
    treatment and prevention of non-complicated senile dementia (290.1);
    treatment and prevention of senile dementia with delirium signs at depression (290.2);
    treatment and prevention of senile dementia with delirium (290.3);
    treatment and prevention of atherosclerotic dementia (290.4).

In another embodiment of the invention, L-Ala-L-Glu-L-Asp-L-Pro tetrapeptide as a drug with nootropic activity, stimulating cerebral repair processes is used as an agent for treatment and prevention of amnestic disorders (294.0) including:
    treatment and prevention of non-alcoholic Korsakoff's psychosis (294.0);
    treatment and prevention of dementia in case of various disorders (294.1) (dementia in HIV-infected patients (HIV-encephalopathy), cerebral lipidosis (330.1), epilepsy (345.0–345.9), syphilis (094.1), hepatolenticular degeneration (275.1), Huntington's (hereditary) chorea (333.4), multiple sclerosis (340) and polyarteritis nodosa (446.0));
    treatment and prevention of a syndrome of chronic non-differentiated organic cerebral lesion (294.9) including AIDS cerebral lesion (042.9).

In another embodiment of the invention, L-Ala-L-Glu-L-Asp-L-Pro tetrapeptide as a drug stimulating cerebral repair processes with cerebroprotective activity is used as an agent for treatment and prevention of multiple sclerosis (340) and other demyelinising cerebral disorders.

In another embodiment of the invention, L-Ala-L-Glu-L-Asp-L-Pro tetrapeptide as a drug with nootropic activity, stimulating cerebral repair processes is used as an agent for treatment and prevention mental deficiency (317–319).

In another embodiment of the invention, L-Ala-L-Glu-L-Asp-L-Pro tetrapeptide as a drug stimulating cerebral repair processes and motional activity is used as an agent for treatment and prevention of paralytic disorders (342–344) including:
 treatment and prevention of hemiplegia (342);
 treatment and prevention of infantile cerebral paralysis (343);
 treatment and prevention of other paralytic syndromes (344) (quadriplegia (344.0), paraplegia (344.1), diplegia of upper extremities (344.2), monoplegia of lower extremities (344.3–344.4)).

In another embodiment of the invention, L-Ala-L-Glu-L-Asp-L-Pro tetrapeptide as a drug stimulating cerebral repair processes with cerebroprotective activity is used as an agent for treatment and prevention of cerebral impairments in case of chromosome anomalies (758) including Down's syndrome.

In another embodiment of the invention, L-Ala-L-Glu-L-Asp-L-Pro tetrapeptide as a drug stimulating cerebral repair processes with cerebroprotective activity is used as an agent for treatment and prevention of cerebral impairments in case of inflammatory cerebral disorders (320–326) including:
 treatment and prevention of cerebral impairments in case of bacterial meningitis (320) including cryptococcus meningitis in AIDS patients;
 treatment and prevention of cerebral impairments in case of non-bacterial meningitis (321);
 treatment and prevention of cerebral impairments in case of meningitis of unclear origin (322);
 treatment and prevention of cerebral impairments in case of encephalitis, myelitis and encephalomyelitis (323), including cerebral toxoplasmosis in AIDS patients;
 treatment and prevention of cerebral impairments in case of intracranial abscesses (324);
 treatment and prevention of cerebral impairments in case of phlebitis and thrombophlebitis of intracranial venous sinus (325);
 treatment and prevention of sequalae after intracranial abscesses or purulent infection (326).

In another embodiment of the invention, L-Ala-L-Glu-L-Asp-L-Pro tetrapeptide as a drug stimulating cerebral repair processes with cerebroprotective and nootropic activity is used as an agent for treatment and prevention of cerebral impairments in case of cerebral-vascular disorders (430–438) including:
 treatment and prevention of cerebral impairments in case of subarachnoid haemorrhage (430);
 treatment and prevention of cerebral impairments in case of cerebral haemorrhage (431);
 treatment and prevention of cerebral impairments in case of occlusion and stenosis of precerebral arteries (433);
 treatment and prevention of cerebral impairments in case of occlusion of cerebral arteries (434);
 treatment and prevention of cerebral impairments in case of transitory cerebral ischemia (435);
 treatment and prevention of cerebral impairments in case of other cerebral-vascular disorders (acute cerebral-vascular disorders (436), cerebral atherosclerosis (437.0) and other generalised cerebral-vascular disorders (437.1), hypertension encephalopathy (437.2), cerebral aneurysm (437.3), cerebral arteritis (472.4) and non-purulent thrombosis of intracranial venous sinus (437.6)).

In another embodiment of the invention, L-Ala-L-Glu-L-Asp-L-Pro tetrapeptide as a drug stimulating cerebral repair processes, having cerebroprotective and nootropic activity is used as an agent for treatment and prevention of alcoholic psychosis (291) including:
 treatment and prevention of delirium tremens at abstinence syndrome (291.1);
 treatment and prevention of alcoholic amnestic syndrome (291.1) and other alcoholic dementia disorders (291.2);
 treatment and prevention of pathologic alcoholic intoxication (291.3);
 treatment and prevention of alcoholic paranoia and alcoholic psychosis of paranoid type (291.5).

In another embodiment of the invention, L-Ala-L-Glu-L-Asp-L-Pro tetrapeptide as a drug stimulating cerebral repair processes, having cerebroprotective and nootropic activity is used as an agent for treatment and prevention of cerebral impairment in case of alcoholism (303).

In another embodiment of the invention, L-Ala-L-Glu-L-Asp-L-Pro tetrapeptide as a drug suppressing toxic effects of neurotropic agents and having cerebroprotective and nootropic activity is used as an agent for treatment and prevention of drug-induced psychosis (292) including:
 treatment and prevention of the drug abstinence syndrome (292.0);
 treatment and prevention of drug-induced paranoid and/or hallucinatory disorders (292.1);
 treatment and prevention of pathologic intoxication with medical agents (292.2);
 treatment and prevention of other drug-induced psychic disorders (292.8) (delirium (292.81), dementia (292.82), amnestic syndrome (292.83) and organic affective syndrome (292.84)).

In another embodiment of the invention, L-Ala-L-Glu-L-Asp-L-Pro tetrapeptide as a drug suppressing toxic effects of neurotropic agents and having cerebroprotective activity is used as an agent for treatment and prevention of drug addiction (304) including:
 treatment and prevention of addiction to opioid agents (304.1);
 treatment and prevention of addiction to barbiturate, sedative agents and tranquilisers (304.1);
 treatment and prevention of cocaine addiction (304.2);
 treatment and prevention of addiction to cannabis derivatives (304.3);
 treatment and prevention of addiction to amphetamine and psychostimulating agents (304.4);
 treatment and prevention of addiction to hallucinogenic agents (304.5);
 treatment and prevention of cerebral impairments caused by drug abuse without drug addiction (305) (abuse of alcohol (305.0), tobacco (305.1), cannabis (305.2), hallucinogens (305.3), opioids (305.5), cocaine (305.6), psychostimulating agents (305.7), antidepressants (305.8)).

In another embodiment of the invention, L-Ala-L-Glu-L-Asp-L-Pro tetrapeptide is used as an agent for treatment and prevention of psychogenic symptoms and syndromes (306–309) including:
 treatment and prevention of psychogenic physiologic impairments (306);
 treatment and prevention of other pyschogenic symptoms and syndromes (306) (stammering and impediments (307.0), psychogenic anorexia (307.1), tics (307.2), repeated stereotype movements (307.3), inorganic sleep disorders (307.4), psychogenic diet disorders (307.5), enuresis (307.7), psychalgia (307.8));

treatment and prevention of acute stress response (308);

treatment and prevention of reactions induced by psychological directions (309).

In another embodiment of the invention, L-Ala-L-Glu-L-Asp-L-Pro tetrapeptide is used as an agent for treatment and prevention of inorganic psychoses (295–299) including:

treatment and prevention of schizophrenic disorders (295);

treatment and prevention of affective psychoses (296);

treatment and prevention of paranoid conditions (297);

treatment and prevention of other inorganic psychoses (298) (psychoses of depressive (298.1) and agitate types (298.2), reactive confusion (298.2), acute paranoid reactions (298.3), psychogenic paranoid psychoses (298.4) and non-differentiated psychoses (298.9) including psychoses induced with cerebral impairments in AIDS patients (042.9));

treatment and prevention of infantile psychoses (299) including infantile autism (299.1) and disintegrative psychoses (299.2).

In another embodiment of the invention, L-Ala-L-Glu-L-Asp-L-Pro tetrapeptide as a drug stimulating cerebral repair processes and having cerebroprotective and nootropic activity is used as an agent for treatment and prevention of cerebral impairments in case of other cerebral disorders (348) including:

treatment and prevention of cerebral impairments in case of cerebral cysts (348.0);

treatment and prevention of hypoxic cerebral damage (348.1);

treatment and prevention of cerebral impairments in case of intracranial hypertension (348.2);

treatment and prevention of cerebral impairments in case of encephalopathy (348.3).

In another embodiment of the invention, L-Ala-L-Glu-L-Asp-L-Pro tetrapeptide as a drug stimulating cerebral repair processes and motional activity, having cerebroprotective and nootropic effects is used as an agent for treatment and prevention of symptoms and syndromes in case of various cerebral disorders including:

treatment and prevention of cognitive disorders, memory and attention impairments (for instance, in case of amnestic diseases, mental deficiency, inorganic psychoses, etc.);

treatment and prevention of aphasia and apraxia (for instance, in case of amnestic diseases, inorganic psychoses, cerebral impairments due to chromosome anomalies, etc.);

treatment and prevention of emotional disorders (for instance, in case of inorganic psychoses, demyelinising cerebral disorders, etc.);

treatment and prevention of psychopathologic syndrome (for instance, in case of transitional organic psychotic conditions, drug-induced psychoses, drug addiction, etc.);

treatment and prevention of asthenic-depressive syndrome (for instance, in case of inorganic psychoses, cerebral impairments due to chromosome anomalies, etc.);

treatment and prevention of delirium syndrome (for instance, in case of drug-induced psychoses and drug addiction, inorganic psychoses, etc.);

treatment and prevention of sleep disorders (for instance, in case of cerebral tumours, transitional organic psychotic conditions, etc.);

treatment and prevention of cerebral-focal syndrome (focal pathologic symptoms) (for instance, in case of cerebral impairments caused by complications of surgical or other medical intervention, demyelinising cerebral disorders, etc.);

treatment and prevention of syndrome of motor disorders (for instance, in case of cerebral tumours, cerebral impairments caused by poisoning, etc.).

Clinical application of the tetrapeptide L-alanyl-L-glutamyl-L-asparagyl-L-proline (L-Ala-L-Glu-L-Asp-L-Pro) confirmed the experimental data on the effectiveness of the said agent in diseases and disorders caused by or associated with the damage or loss of cerebral neurones.

The below-listed examples of the clinical trials on the proposed tetrapeptide demonstrate the pharmacological properties thereof and confirm the possibility to implement the invention.

Example 10

Efficacy of Applying L-Ala-L-Glu-L-Asp-L-Pro Tetrapeptide in Case of Craniocerebral Injury Complications The trial was conducted on 35 patients with remote complications of craniocerebral injury. They were divided into 3 groups: a control one (10 patients—standard treatment), a group under study (15 patients—standard treatment+1 µg of L-Ala-L-Glu-L-Asp-L-Pro tetrapeptide intramuscularly, daily for 10 days) and a comparison group (10 patients—standard treatment+Cerebrolysin). Remoteness of the suffered craniocerebral injury in the patients constituted 1 to 10 years. Decompensation of the posttraumatic process occurred in all the patients and was manifested in liquorodynamic disorder, neurocirculatory dystonia, cerebrofocal and psychopathologic syndromes.

Effect of the treatment with L-Ala-L-Glu-L-Asp-L-Pro tetrapeptide on the patients' attention was assessed by the proof test before and after the treatment. Significant increase in the number of reviewed symbols and decreased number of mistakes was noted, which indicated enhanced attention and raised stability of attention promoted by the tetrapeptide action (Table 5).

In the patients treated with the tetrapeptide better results were obtained on the analysis of changes in the proof test before and after the therapy, in comparison with the patients in other groups. It was manifested in the absence of sharp fluctuations in the number of reviewed symbols during equal periods of time, in the "accommodation" period at the middle of the task execution and in a gradual decline of the curve by the end of the task, which indicated a greater stability of attention after the treatment with the present agent.

TABLE 5

Effect of L-Ala-L-Glu-L-Asp-L-Pro tetrapeptide on the indices of the proof test performance

| Groups of patients | Reviewed symbols | Number of mistakes |
|---|---|---|
| Healthy Volunteers | 2969.6 ± 91.2 | 2.6 ± 0.3 |
| Patients before the treatment | 1505.1 ± 134.7 | 12.9 ± 1.5 |
| Conventional treatment | 1977.4 ± 186.4 | 10.5 ± 1.9 |

TABLE 5-continued

Effect of L-Ala-L-Glu-L-Asp-L-Pro tetrapeptide on the indices of the proof test performance

| Groups of patients | Reviewed symbols | Number of mistakes |
|---|---|---|
| Conventional treatment + Cerebrolysin | 2193.3 ± 120.6 | 9.4 ± 1.7 |
| Conventional treatment + L-Ala-L-Glu-L-Asp-L-Pro tetrapeptide | 2519.6 ± 105.3* | 6.3 ± 1.1* |

*$P < 0.05$ in comparison with the results of conventional treatment.

To assess the influence of L-Ala-L-Glu-L-Asp-L-Pro tetrapeptide on the cerebral bioelectric activity, a visual EEG (electroencephalography) test was carried out with its distribution on types and calculation of α-index before and after the treatment. EEG test was selectively performed in the patients from different groups showing most notable signs of disorder.

Before the treatment patients pathologic (III, IV and V) types of EEG prevailed in all the groups. The III-rd EEG type was characterised by the presence of so-called "non-dominant" curve, alongside with a low amplitude rate (no higher than 30–35 μV), irregular or even absent α-activity. The IV-th EEG type was marked by an extremely emphasised rhythm regularity and blurred zonal differences. The V-th EEG type was represented with an irregular slow activity (amplitude exceeding 35 μV), sharp waves and paroxysmal discharges.

The most pronounced changes in the cerebral bioelectric activity were registered in the patients treated with the tetrapeptide that was manifested in EEG by, mainly, more distinct modulating and restoration of α-rhythm zonal differences, reduced exhibition of irritating processes and, in some cases, disappearance of paroxysmal discharges.

The treatment was found to have a significantly increasing effect on the α-index in the studied patients. However, degree of the α-index changes in the patients with different therapy regimens varied. The α-index change was significantly higher in the patients treated with the present tetrapeptide comparing to parameters in other groups.

TABLE 6

Effect of L-Ala-L-Glu-L-Asp-L-Pro tetrapeptide on the α-index EEG variation in the patients

| Patient groups | α-index |
|---|---|
| Healthy volunteers | 52.9 ± 3.2 |
| Patients before treatment | 35.7 ± 4.6* |
| Conventional treatment | 39.6 ± 4.1*** |
| Conventional treatment + Cerebrolysin | 42.4 ± 3.9*** |
| Conventional treatment + L-Ala-L-Glu-L-Asp-L-Pro tetrapeptide | 47.9 ± 3.1** |

*$P < 0.05$ in comparison with the indices in the healthy volunteers.
*$P < 0.05$ in comparison with the indices before the treatment.

The obtained data indicated a significant increase in the α-index in all the studied groups and, simultaneously, a more considerable increase in the said index in the patients treated with the tetrapeptide.

Comparison of the subjective indices of the patients' state before and after the treatment with the tetrapeptide showed memory and mental agility improvements, reduction in the intensity and duration of headaches, emotional evenness, will activity and recovery after a night repose in 71% of the cases.

Thus, the following therapeutic effects of L-Ala-L-Glu-L-Asp-L-Pro tetrapeptide administration in the patients with last sequalae of the craniocerebral injury in period of post-traumatic process decompensation: improvement in the cognitive functions of the brain, memory and attention, restoration of the cerebral bioelectric activity.

Example 11

Efficacy of L-Ala-L-Glu-L-Asp-L-Pro Tetrapeptide in the Treatment for Vascular Dementia Twelve patients aged 69 to 76 years (7 males and 5 females) suffering from hypertensive disease and atherosclerosis of cerebral vessels for a long time were enrolled in the study. Three of them had apoplexy in their medical histories. Initial data obtained in the similar patients before the treatment was used as control. L-Ala-L-Glu-L-Asp-L-Pro tetrapeptide was intramuscularly injected in a single dose of 3 μg once daily for 30 days.

Results were assessed after the treatment in comparison with the data obtained before the treatment. Basing on the examination results, changes in the patients' state were defined according to the following gradation: improvement (substantial, average or minor), deterioration, no changes.

At the pretreatment examination signs of intellectual-mnemic defect were found in all the patients: memory impairment, intellectual deterioration, aphasia, apraxia and agraphia disorders. In 9 patients signs of disorientation in time and place were found. The patients' emotional state was labile, manifested with periodical alternation of apathy and euphoria, complacency and anger aptness. The psychological examination showed that there were notable impairments of memory and ability of efficient intellectual activity, aphasia.

The clinical state improved by 4–5$^{th}$ day. Improved activity and intention for some action were noted, the patients stayed in bed less and their emotional instability reduced. On the 5–7$^{th}$ days their sleep normalised, fatigue at execution reduced, the patients better oriented in the environment. Signs of amnesia, aphasia and apraxia diminished. Moreover, their ability to reproduce previous experience and memory for current events improved. The emotional state changes depended on their previous emotional background. Patients with depression noted improvements in the mood along with an enhanced general tonus and better somatic state; apathetic patients became more active. In cases of emotional lability and enhanced irritability, emotional state of the patients became more stable in the course of the treatment.

Neuropsychological and psychophysiological examinations showed that under action of the tetrapeptide there were noted improved short memory, focusing, increased amount of memorised information. Moreover, the patients exhibited shortening of time for arithmetic calculations along with decreased number of mistakes. After the treatment the patients manifested significant increase of attention span and also parameters of complicated sensomotor reaction with selection improved.

Thus, preliminary clinical trial of L-Ala-L-Glu-L-Asp-L-Pro tetrapeptide in the patients with vascular dementia showed a significant therapeutic effect of the preparation, because in the course of applied treatment with low drug dosage 74.8% of the patients showed reverse development of the pathologic symptoms.

The displayed data indicate high effectiveness of L-Ala-L-Glu-L-Asp-L-Pro tetrapeptide in cases of cognitive impairment, memory and attention disorders, aphasia, apraxia and emotional disorders in the patients with vascular dementia.

REFERENCES

1. Mashkovsky M. D. Therapeutic Agents. Manual on Pharmacotherapy for Medical Doctors. 2 Vol.—Vilnius, 1993. V. 1—P. 101–110.
2. Korsching S. The Neurotropic Factor Concept: a Reexamination//Neuroscience.—1991.-Vol. 13, NY—P. 2739.
3. Maschkovsky M. D. Therapeutic Agents. Manual on Pharmacotherapy for Medical Doctors. 2 Vol.—Vilnius, 1993. V. 2—P. 84–88.
4. Krivitskaya G. N., Gelfand V. B., Popova E. N. Destructive and Reparative Processes at Focal Cerebral Impairments.—M., Medicine, 1980—214 p.
5. Nesmeyanova T. N. Stimulation of Repair Processes at Spinal Cord Trauma.—Moscow, Nauka, 1971—255 p.
6. Krighanovski G. N., Karaban I. N., Magayeva S. V. et al. Compensatory and Repair Processes in Parkinsonism.—Kiev: Academy of Medical Sciences of the Ukraine, 1995—186 p.
7. Ernfors P., Ivanez C. F., Ebendal T. Molecular Cloning and Neurotropic Activities of a Protein with Structural Similarities to Nerve Growth Factor; Developmental and Topographical Expression in the Brain//Proc. Natl. Acad. Sci. USA.—1990—Vol. 87, N9—P. 5454–5458.
8. Elde R., Cao Y., Cintra A. Prominent Expression of Acidic Fibroblast Growth Factor in Motor and Sensor Neurons// Neuron—1991—Vol. 7, N 8—P. 349–364.
9. Jakubke H. -D., Eshkeit H. Amino Acids, Peptides, Proteins: translated from German—Moscow: Mir, 1985—456 p.
10. Teppermen J., Teppermen H. Physiology of Metabolism and Endocrine System: translated from English—Moscow: Mir, 1989—656 p.
11. Bakharev V. D. Clinical Neurophysiology of Regulatory Peptides.—Sverdlovsk: Publishing House of the Ural Institute, 1989—136 p.
12. Morozov V., Khavinson V. Achievement and prospects in the field of bioregulation and gerontology//Materials of Int. Symp. "Gerontological Aspects of Peptide Regulation of Organism Functions"—1996—St. Petersburg—P. 105–107.
13. Khavinson, V., Chalisova N., Okulov V. The neurite-stimulating effect of peptides from brain in dorsal root ganglion neuron organotypic culture//Primary Sens Neuron—1997—Vol. 2 (3)—P. 191–200.
14. International Classification of Diseases, 9th Revision—Washington—1989.

The invention claimed is:

1. A Tetrapeptide L-alanyl-L-glutamyl-L-asparagyl-L-proline of the general formula L-Ala-L-Glu-L-Asp-L-Pro (SEQ ID NO:1).

2. The Tetrapeptide L-alanyl-L-glutamyl-L-asparagyl-L-proline of the general formula L-Ala-L-Glu-L-Asp-L-Pro (SEQ ID NO:1), as an agent stimulating the functional activity of neurones.

3. A Pharmacological agent stimulating the functional activity of neurones, containing an active base and a pharmaceutically admissible carrier, comprising an effective amount of L-Ala-L-Glu-L-Asp-L-Pro (SEQ ID NO:1) tetrapeptide or its salts.

4. The agent described in claim 3, comprising salts of the amino acid group.

5. The agent of claim 3, comprising salts of carboxyl groups or the salts of organic and inorganic cations.

6. The agent of claim 3, provided in a formulation for parenteral administration.

7. The agent of claim 3, provided in a formulation for intranasal administration.

8. The agent of claim 3, provided in a formulation for oral administration.

9. The method of stimulating the functional activity of neurones, comprising a step of administering to the patient an effective amount of L-Ala-L-Glu-L-Asp-L-Pro (SEQ ID NO:1) tetrapeptide or a salt thereof in a dose in a range of 0.01 to 100 µg/kg of the body weight at least once a day for a period necessary for attaining a therapeutic effect.

10. The method of claim 9 wherein the step of administering the effective amount is by administering parenterally, intranasally or orally.

11. A method for stimulating cerebral repair in a patient in need thereof, comprising the step of providing said patient with a sufficient amount of L-Ala-L-Glu-L-Asp-L-Pro (SEQ ID NO:1) tetrapeptide to stimulate cerebral repair.

* * * * *

---

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Tetrapeptide Ala Glu Asp Pro stimulates the
      neuronal functional activity in the central and peripherical
      nervous system due to the metabolic processes normalisation.

<400> SEQUENCE: 1

Ala Glu Asp Pro
1
```